(12) United States Patent
Acuna Llanes

(10) Patent No.: US 9,862,911 B2
(45) Date of Patent: Jan. 9, 2018

(54) SYSTEM AND PROCESS FOR PALM OIL EXTRACTION BY CRACKING, THRESHING AND DYNAMIC STERILIZATION OF THE FRESH FRUIT

(71) Applicant: Phina Biosoluciones S.A.S., Bucaramanga-Santander (CO)

(72) Inventor: Angel Custodio Acuna Llanes, Bucaramanga-Santander (CO)

(73) Assignee: Industrias Acuña Ltda., Bucaramanga (CO)

( * ) Notice: Subject to any disclaimer, the term of this patent is extended or adjusted under 35 U.S.C. 154(b) by 0 days.

(21) Appl. No.: 15/074,516

(22) Filed: Mar. 18, 2016

(65) Prior Publication Data

US 2016/0201008 A1 Jul. 14, 2016

Related U.S. Application Data

(63) Continuation of application No. PCT/CO2014/000011, filed on Sep. 24, 2014.

(30) Foreign Application Priority Data

Sep. 30, 2013 (CO) ............................ 13-0231.985

(51) Int. Cl.
| | |
|---|---|
| *C11B 1/10* | (2006.01) |
| *A61L 2/07* | (2006.01) |
| *B65G 65/30* | (2006.01) |
| *C11B 7/00* | (2006.01) |
| *A23N 5/00* | (2006.01) |
| *B02C 13/00* | (2006.01) |

(52) U.S. Cl.
CPC ............... *C11B 1/10* (2013.01); *A61L 2/07* (2013.01); *B65G 65/30* (2013.01); *C11B 7/0075* (2013.01); *C11B 7/0083* (2013.01); *A23N 5/004* (2013.01); *B02C 13/00* (2013.01)

(58) Field of Classification Search
None
See application file for complete search history.

(56) References Cited

U.S. PATENT DOCUMENTS 5,039,455 A * 8/1991 Kooi ..................... C11B 1/04
554/17

FOREIGN PATENT DOCUMENTS

| GB | 1474367 | * | 5/1977 | ............... C11B 1/00 |
| GB | 2421169 | * | 6/2006 | ............... C11B 1/04 |
| WO | WO 2012/096561 | * | 7/2012 | ............... C11B 1/06 |

* cited by examiner

*Primary Examiner* — Yate K Cutliff
(74) *Attorney, Agent, or Firm* — Baker Hostetler LLP

(57) ABSTRACT

The present invention patent application belongs to the field of mechanical engineering and consists of a system and process for palm oil extraction integrally configured for processing the entire fresh fruit (rachis, spikes and seeds or fruits) by stages of cracking, threshing, dynamic sterilization and subsequent pressing. Said disclosed system and process allow increasing the percentage of oil extraction with less equipment and a smaller workspace compared to that required by the already known conventional processes, as well as using smaller amounts of water and energy. Additionally, the disclosed system and process allow obtaining sterilized plant material with low humidity, which may be used as organic matter for composting or as fuel of the extraction system itself.

17 Claims, 18 Drawing Sheets

SYSTEM AND PROCESS FOR PALM OIL EXTRACTION BY CRACKING, THRESHING AND DYNAMIC STERILIZATION OF THE FRESH FRUIT

CROSS REFERENCE TO PRIOR APPLICATIONS

This application is a continuation of International Application No. PCT/CO2014/000011, filed Sep. 24, 2014 and designating the U.S., which claims priority to Colombian Patent Application No. CO 13-0231.985, filed Sep. 30, 2013, both of which are incorporated herein by reference in their entirety.

BACKGROUND OF THE DISCLOSURE

Field

Mechanical Engineering. Production of vegetable oils by raw material pressing or by extracting waste material (C11B 1/00).

Technical Background

The marked importance of palm oil as raw material in the manufacture of food products, personal care products and in the production of biodiesel, among others, has led the extraction process of the palm fruit to be subject of permanent research, and therefore diverse systems and processes for palm oil extraction are currently known in the state of the art.

In this manner, for instance, nowadays the called 'conventional systems' are known for the palm oil extraction, which are basically characterized in that:

The sterilization process is performed statically and with the whole fruit (formed by the rachis and the seeds) by deposit in rail wagons for introduction into the sterilizer, which requires large areas for handling this equipment.

Additionally, said static sterilization is characterized by involving water consumption in the range between 800 liters and 1000 liters per processed tonne, sterilization times between 60 and 70 minutes, and an intermediate step between the sterilization and digestion processes that consists in separating fruits from rachis, already sterilized in rotating drums that contain the rachis with high levels of oil impregnation and attached fruit, fact that undoubtedly represents a high percentage of oil loss and also becomes an element of environmental pollution.

Fruits that are sterilized and separated from the rachis should undergo a digestion process through mechanical stirring and steaming for about 20 minutes, the above with the purpose that the fruits recover the lost temperature during the phase of separation from the rachis.

Once digestion is completed, fruits are subjected to a process of conventional pressing, where the liquid phase is released with a high solid content and therefore it is necessary to use equipment having greater capacity for oil clarification and obtention. In turn, the solid phase resulting from the pressing process has high humidity (up to 40%) due to the filtering medium generated in the press by the mesocarp fibers whose size does not exceed 4 mm.

Finally, the use of conventional systems for palm oil extraction involves the presence of sludge in the final effluent, requiring the implementation of large pools for their treatment.

On the other hand, 'dynamic systems and processes' for palm oil extraction are also known in the state of the art, such as those disclosed in the Colombian Patent CO 09-100.228, and which are characterized in that:

There is a first step of cracking and threshing of the whole fresh fruit, after which the spikes and rachis from detached fruits containing oil to be extracted are separated. Unfortunately, said process drags a great amount of fruit that remains attached to the rachis, causing excessive oil leaks.

Spikes and chopped rachis are pressed without having been subjected to a sterilization process, with which fruit gums that affect quality of the oil are obtained, as well as fibers with high crude oil impregnation whose acidification is evident and detrimental for the extra oil obtained. Additionally, pressing the fiber separately increases energy and equipment requirements, while vegetable fibers are exposed to fast putrefaction as a result of exposure to the environment.

The process of sterilization of the detached fruits containing the oil to extract is carried out by sterilizer equipment comprising inlet and discharge of the product valves with double gates for continuous sterilization, design that leads to serious issues due to the low capacity of processing of oil palm fruit.

The stirring system inside the sterilizers does not allow optimal stirring of the product because it uses a continuous helix with some agitation blades simply moving the product from the inlet towards the outlet of the sterilizer, but failing to produce a complete digestion of the product resulting in an optimal dynamic sterilization process.

Considering the above, it is evident that there is a need in the state of the art for developing a system and a process for palm oil extraction allowing to overcome the technical problems encountered with the use of the currently known systems and methods, redesigning the system equipment and the steps of the extraction process to reduce process costs and increase the quality of the obtained product.

SUMMARY OF THE DISCLOSURE

Taking into account the teachings of the prior art and based on the technical features of the different systems and processes known in the prior art that have been created to achieve palm oil extraction, the applicant of the present invention has developed a novel system that incorporates several mechanical equipment specifically concatenated and allows to implement a new process for processing the fresh fruit of the oil palm.

Indeed, according to the present invention the product to be processed is arranged in a receiving hopper responsible for dosing the product to a conveyor system that leads it to a cracking and threshing tower, where initially the crack of rachis is achieved and the detachment of about 40% of fresh fruits (which are sent to a further system of transport after passing through a fixed grid) and subsequently the cracking rachis is treated in a threshing machine, in which, by the action of rotating metallic elements, the entirety of the cluster is mechanically broken.

The entirety of the product obtained in the preceding step is then sent to a transport system that leads it to a battery of dynamic sterilizers arranged in parallel, where the product is deposited inside of each of the dynamic sterilizers by the continuous and rotary action on its shaft, disposed centrally and provided with two helical bands with different diameters and opposite directions that facilitates loading and unloading of the product, simultaneously performing the sterilization process and digestion of the fruit.

In this sense, the cracked and shelled fresh fruit is placed inside each dynamic sterilizer through a curtain valve arranged in the top of the sterilizer top to fill between 60% and 70% of the internal volume, after which the mentioned curtain valve is closed and the sterilization and digestion process starts by applying steam to reach a maximum temperature of 140° C. and an internal pressure in the range between 30 and 50 PSI.

The sterilizers are filled and pressurized in a sequential manner, maintaining the rotation of the central shaft in one direction while the conditions of temperature and pressure required are achieved, but leading to the movement of said rotation shaft in both directions once said temperature and pressure conditions are achieved. Said mechanical action results in a dynamic sterilization process based on the constant movement of the fruit inside the sterilizer during the time expected for completing the process, which ranges between 25 and 40 minutes depending on the conditions and quality of the steam.

It should be noted that the condensates produced into each of the sterilizers are evacuated and transported to a pre-clarifier for the recovery of oil entrained.

Now, once the unified sterilization and digestion process is made, the product is discharged and driven by a conveyor system specifically configured to lift the product to a suitable height above a live bottom vessel located above a press for red oil extraction, after which all the material is subjected to pressing.

The liquid phase obtained from pressing and formed by oil, water and suspended solids is discharged to a vibrating screen, obtaining a sieved press liquor that is driven to the clarifier where the separation of oil is performed. In turn, solids obtained in the vibrating screen are conveniently transported for reprocessing into the red oil press.

Finally, the solid phase obtained in the press after reprocessing and formed by chopped rachis total fibers, mesocarp fibers and nuts of the fruit is deposited on a conveyor dryer cake, so once a dried cake is obtained, is placed in an air separation column for separating the total dried fibers from the nuts, which are evacuated through a nut polishing drum. On the other hand, the fibers obtained in the air separation column are available to be used in the steam generator boiler, or to be incorporated in composting processes.

In this manner, the system and process disclosed in the present invention allow solving satisfactorily all the technical problems that commonly arise with the systems and methods for extracting palm oil known in the prior state of the art, turning into optimal mechanisms to carry out palm oil extraction.

BRIEF DESCRIPTION OF THE DRAWINGS

In addition to the above, the subject matter of the present application and the technical advantages achieved by the inventor may be appreciated in detail through the following description of the system and process disclosed herein with reference to the accompanying drawings, in which.

DETAILED DESCRIPTION OF THE INVENTION

Figure 1:
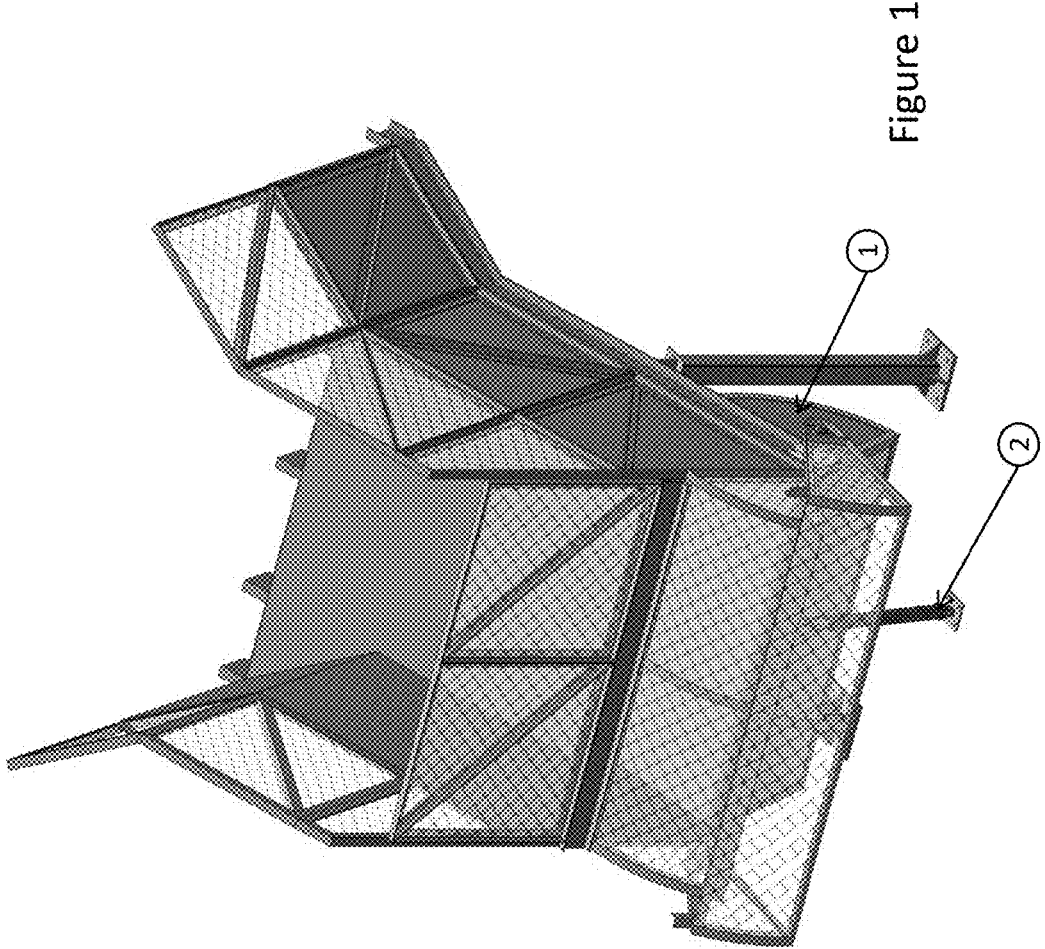
FIG. 1 corresponds to a diagram of the receiving hopper of fresh whole fruit.
Figure 2:
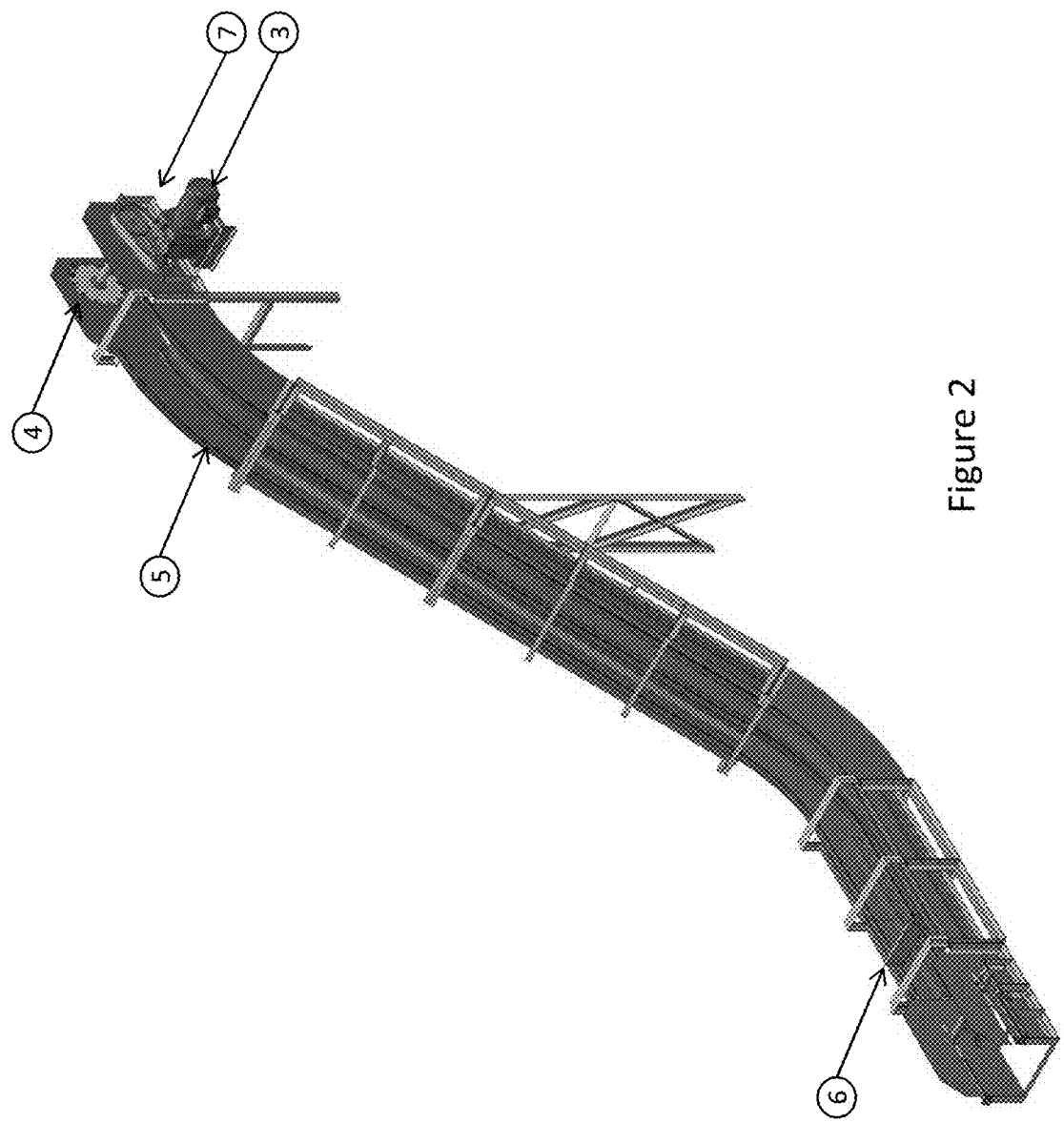
FIG. 2 corresponds to a diagram of the fresh whole fruit conveyor.
Figure 3:
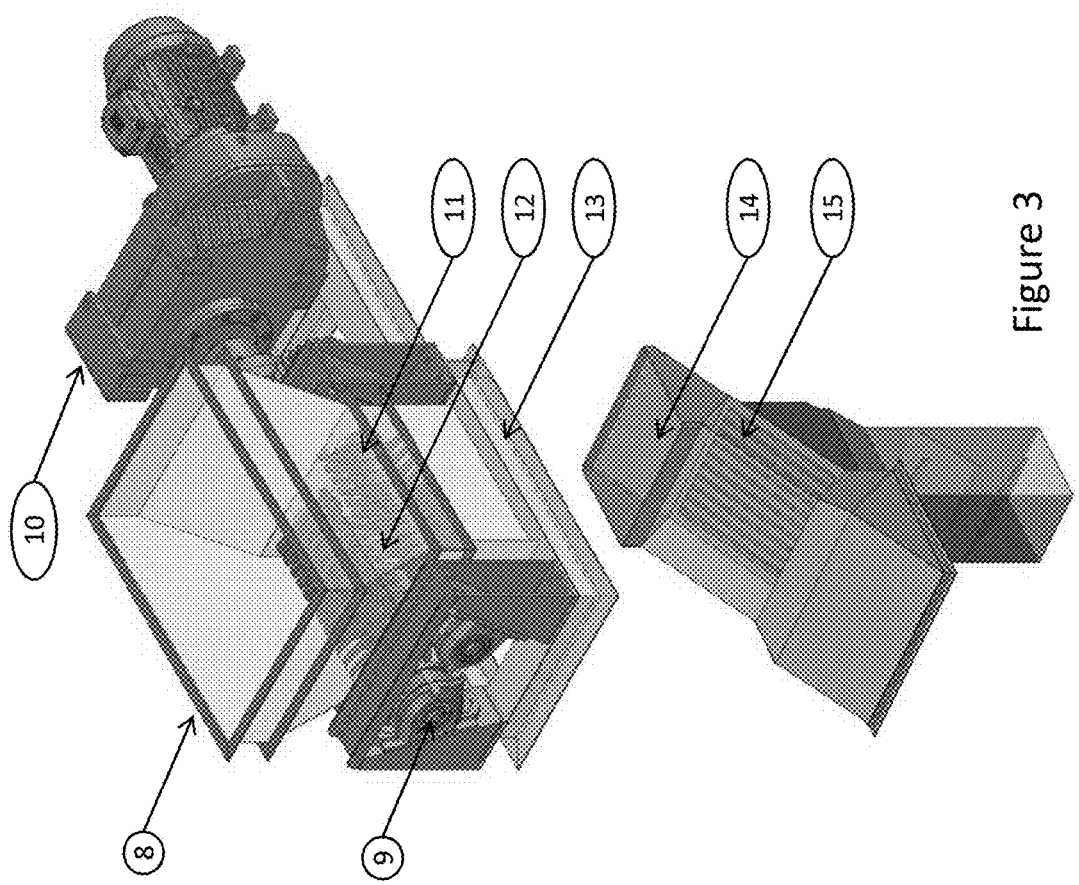
FIG. 3 corresponds to a diagram of the cracking apparatus.

Now, regarding FIG. 1, the fresh fruit in bunch is deposited inside the receiving hopper which has a metering mechanism consisting of a flat or curved plate 1 that is moved by the action of a hydraulic cylinder 2, allowing dosed and controlled passage of the fruit through the entrance of the hopper to deliver the material to the conveyor of FIG. 2 which in turn leads it to the cracking apparatus of FIG. 3.

Said conveyor mechanism contains in its lower part a system attached to the hopper for receiving the whole fruit, and is actuated by a gearmotor 3 which rotates a shaft adapted to a driving pinion 4, which in turn shifts chain 5, which by action of transverse plates 6 moves fruits to the next step of the process. The conveyor has an outlet 7 where the detached fruits are naturally discharged.

Figure 4:
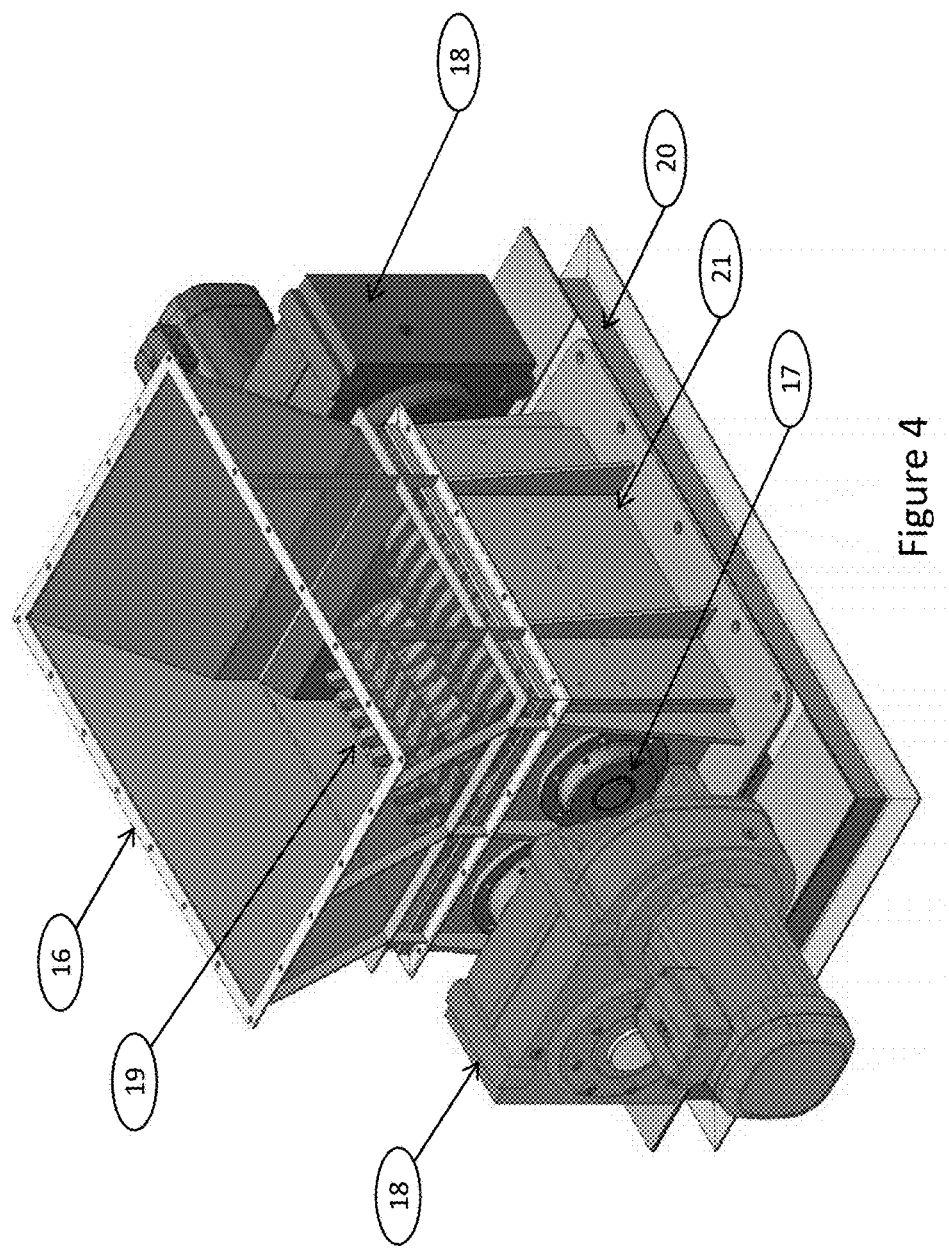
FIG. 4 is a diagram of the threshing apparatus.

In turn, the cracking machine of FIG. 3 has a fruit receiving hopper 8 and in its middle part has two shafts 9, which are actuated by a gearmotor 10. Said shafts 9 have installed a series of mechanical devices formed by rotating nails 11 which make the rotor turn at different speeds and allow cracking the entirety of the bunch with a central blade 12 disposed between both shafts. These mechanical elements are supported by a main structure 13 and have a lower outlet hopper 14 for delivering the fractured material onto an inclined grid 15 which consists of several plates installed diagonally and which are spaced to allow direct passage of the detached fruits and at the same time guide the movement of cracking fruits towards the threshing apparatus of FIG. 4.

Said threshing apparatus together with the cracking apparatus are located and arranged in a structure so as to allow a regular flow of the processed material.

Now, the threshing apparatus is characterized in that its upper part has a hopper 16 which receives the cracked fruits and in its middle part contains two shafts 17 that rotate by action of two gearmotors 18 at different rotation speeds. Additionally, over the shafts, various mechanical means 19 are located, which consist of nails with different size that thresh the fruits attached to the cracked bunches during their rotational movement. The rotating members 17 and gearmotors 18 are located on a main frame 20 which in its lower part has an outlet hopper 21 for delivering threshed material to the next conveyor system.

Figure 5:
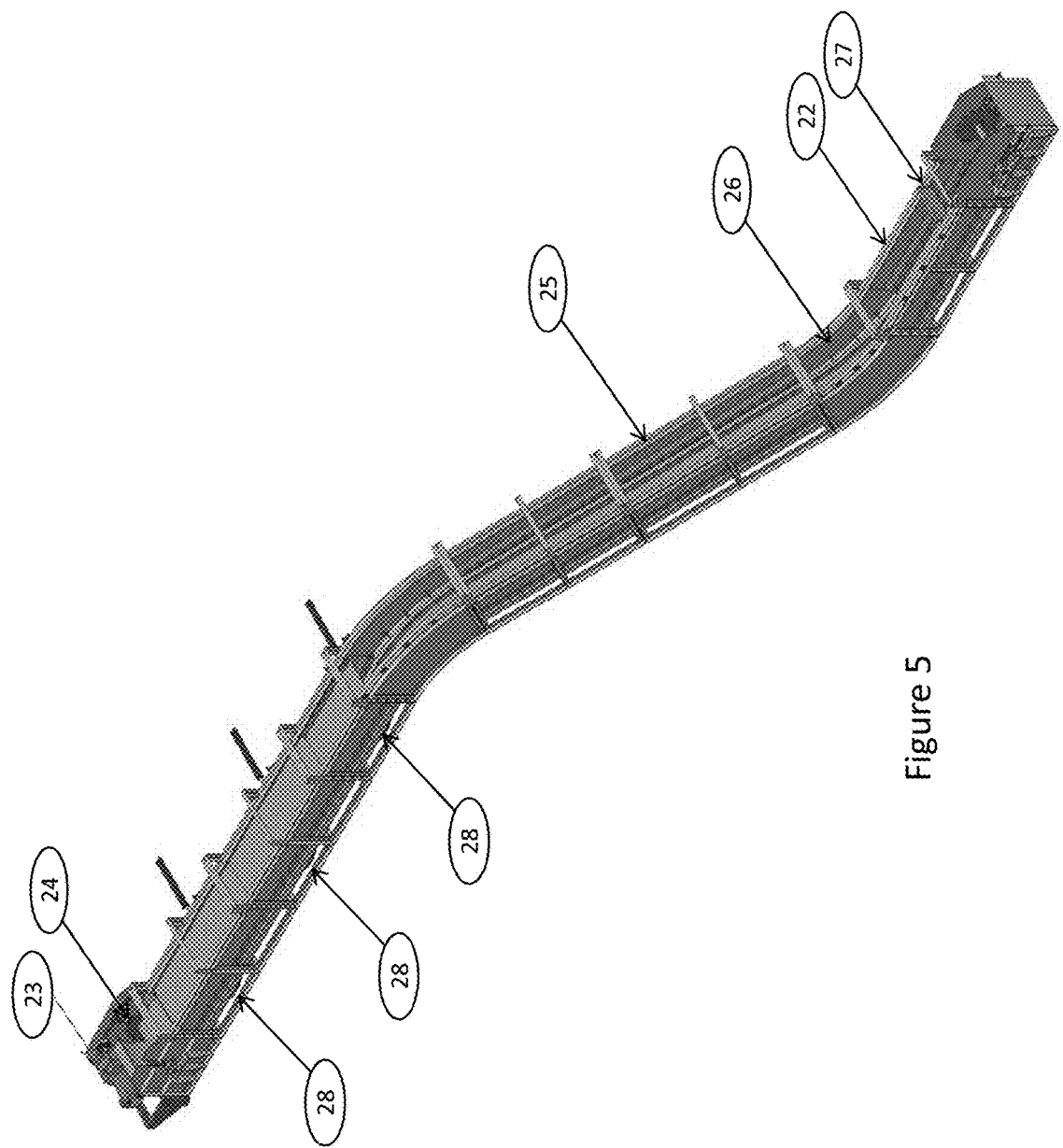
FIG. 5 corresponds to a diagram of the cracking/threshed fruit conveyor.

The conveyor of cracked/threshed fruit of FIG. 5 is responsible for receiving the processed fruit and later moving it to the battery of dynamic sterilizers. Said conveyor has in its lower part a fastening system 22 to connect to the lower part of the threshing apparatus and is actuated by a gearmotor 23 which in turn actuates a central shaft provided with a chain pinion 24 that by rotation moves the chain 25 by sliding it into the main body of equipment 26. In addition, a plurality of transverse plates 27 attached to the chain receive the fruit and move it to the upper part, where through a gate 28 deliver the product to any of the dynamic sterilizers for the next process.

Figure 6:
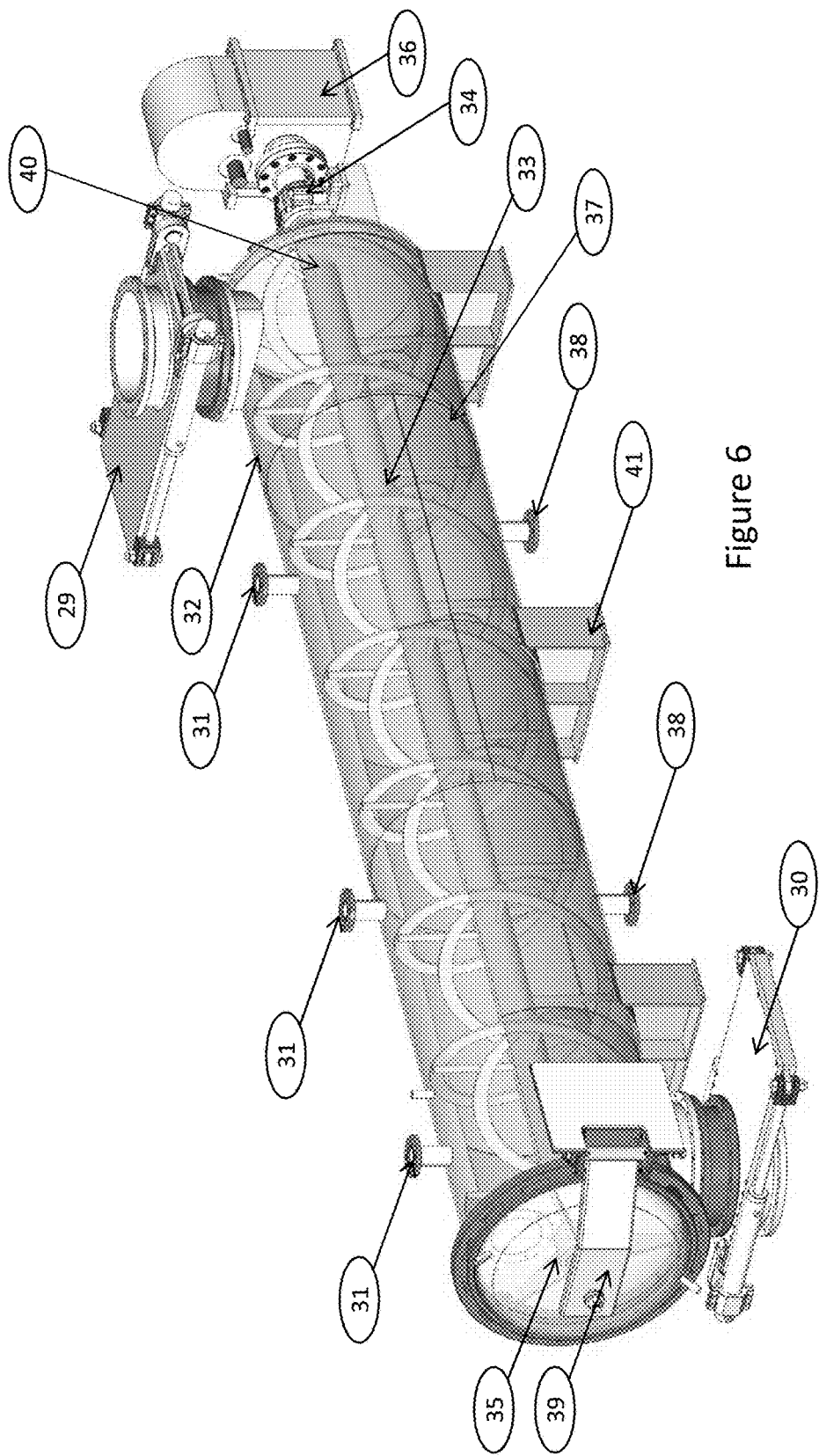
FIG. 6 shows a dynamic sterilizer according to the invention, including a view of the central shaft and helical bands set.

Now, said dynamic sterilizer of FIG. 6 is a cylindrical vessel designed to withstand pressures up to 100 psi and temperatures up to 200° C., has an intake valve 29 installed on the top to receive the fruit delivered by the conveyor of FIG. 5, and also has at the lower part an outlet valve 30. Valves 29 and 30 are arranged to be closed during the sterilization and digestion process made with steam coming from a boiler and injected through inlets 31 located in the upper part of the sterilizer cylinder.

At this point it is important to note that the temperature, pressure and time conditions are determined in accordance with the quality of the fruit entered to each sterilizer.

In the center of each sterilizer cylinder and along the main body 32 is a central shaft 33 which is supported at one end by a support bearing 34 and at the other end by a support bearing 35, while the shaft end is actuated by a gearmotor 36 which rotates the shaft at different speeds. The central shaft has around a set of helical bands 37, an external band of right direction and an internal band of left direction that provides the equipment with the load, unload and rotation system for the material to be processed and that is constituted by the circular movement clockwise and counterclockwise in the sterilization dynamics process applied to the fruit to extract the oil.

In the bottom of the sterilizer flanged outlets 38 are disposed for evacuating the condensate generated during the sterilization process. To control the steam and condensate discharge, the system is provided with fluid control valves that are located on these sites of the equipment.

A cap attached to the body 39 is located in the front part of the sterilizer to facilitate the work of assembly and inspection of the equipment for maintenance. On the other hand, for internal sealing, the sterilizer has a pressure switch 40 built on a metal support with its own hub and special seal cord for high temperatures and pressures. All the sterilizer is supported on metal brackets 41 and is installed on a metal structure.

Dynamic sterilizers that are part of the system disclosed in the present invention are installed in parallel alignment to facilitate the processes of product loading and unloading. The amount of sterilizers included in a particular plant is determined from the total fruit processing capacity. For different capacities, said sterilizers may be constructed in different diameters and lengths depending on the capacity process requirements of the set.

The dynamic sterilization system allows optimizing the use of water resources necessary to produce steam, because when performing the dynamic rotational motion the natural water the product has is hydrolyzed.

The general process includes the steps of receiving the material, filling the sterilizer, dynamic stirring, closing valves, steam injection, reaching of temperature and pressure conditions, maintaining conditions, condensate removal, steam evacuation, valve opening and final product evacuation by rotating action of the shaft through the outlet valve 30.

Figure 7:
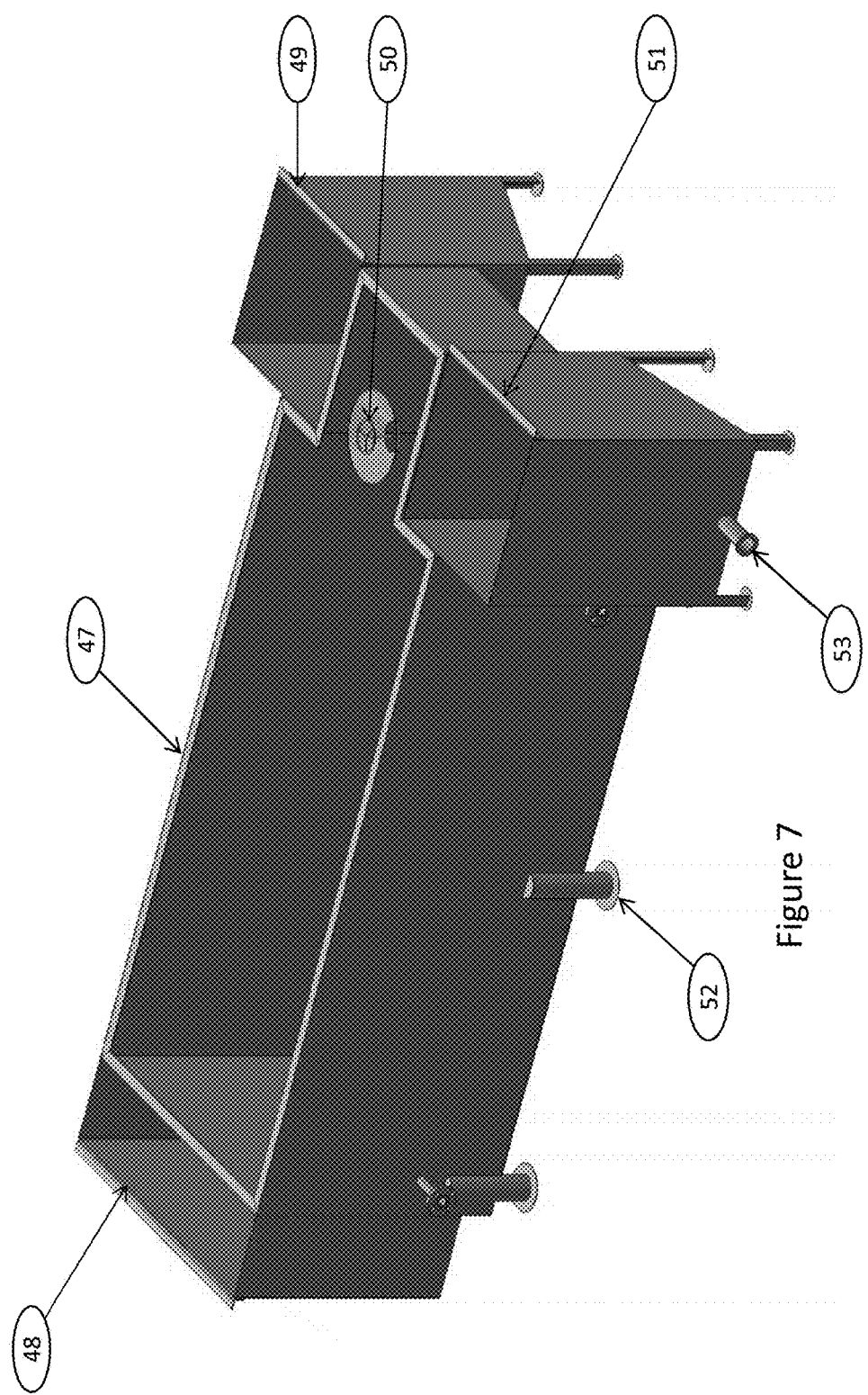
FIG. 7 corresponds to a diagram of the pre-clarifier.

On the other hand, the pre-clarifier of FIG. 7 is a rectangular container whose main body 47 is formed by reinforced steel sheets with structural profiles. At one end it has a container 48 for receiving condensates and press liquor from the vibrating screen, while in the internal part has a tube-made grid configured to heat the liquid using steam.

On the front side of said pre-clarifier a rectangular tank 49 is arranged, responsible for receiving the pre-clarified oil through discharge plates 50. In addition, the pre-clarifier has another rectangular tank 51, which is responsible for receiving the muddy water resulting from the process of clarifying the press liquor.

The pre-clarifier in its entirety relies on metal supports 52 and each rectangular container contains a flanged outlet 53 provided for directing the oil and the muddy water to the subsequent processes of dehydration and clarification treatment.

Figure 8:
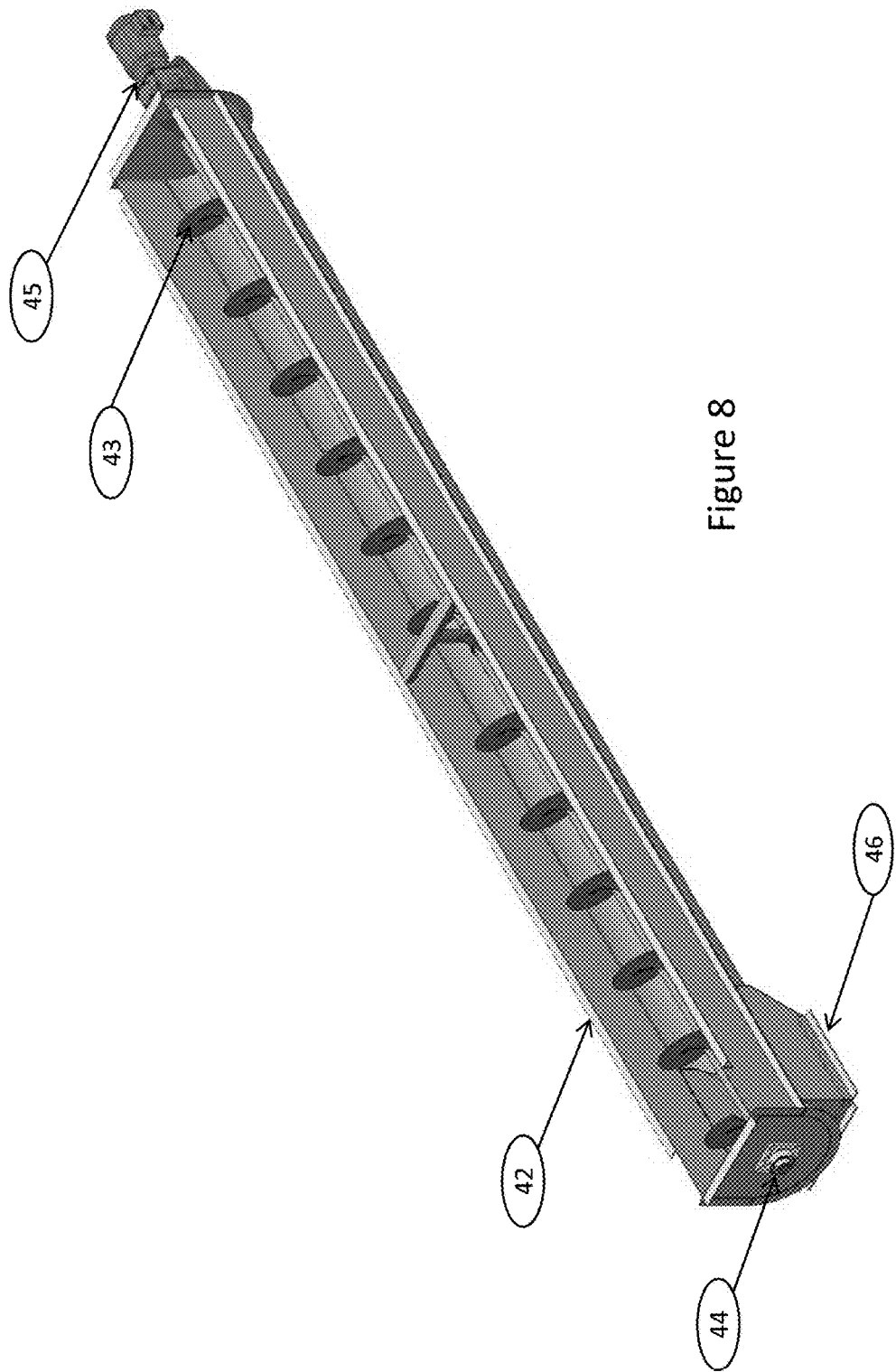
FIG. 8 corresponds to a general view of the conveyor used to discharge sterilizers.
Figure 9:
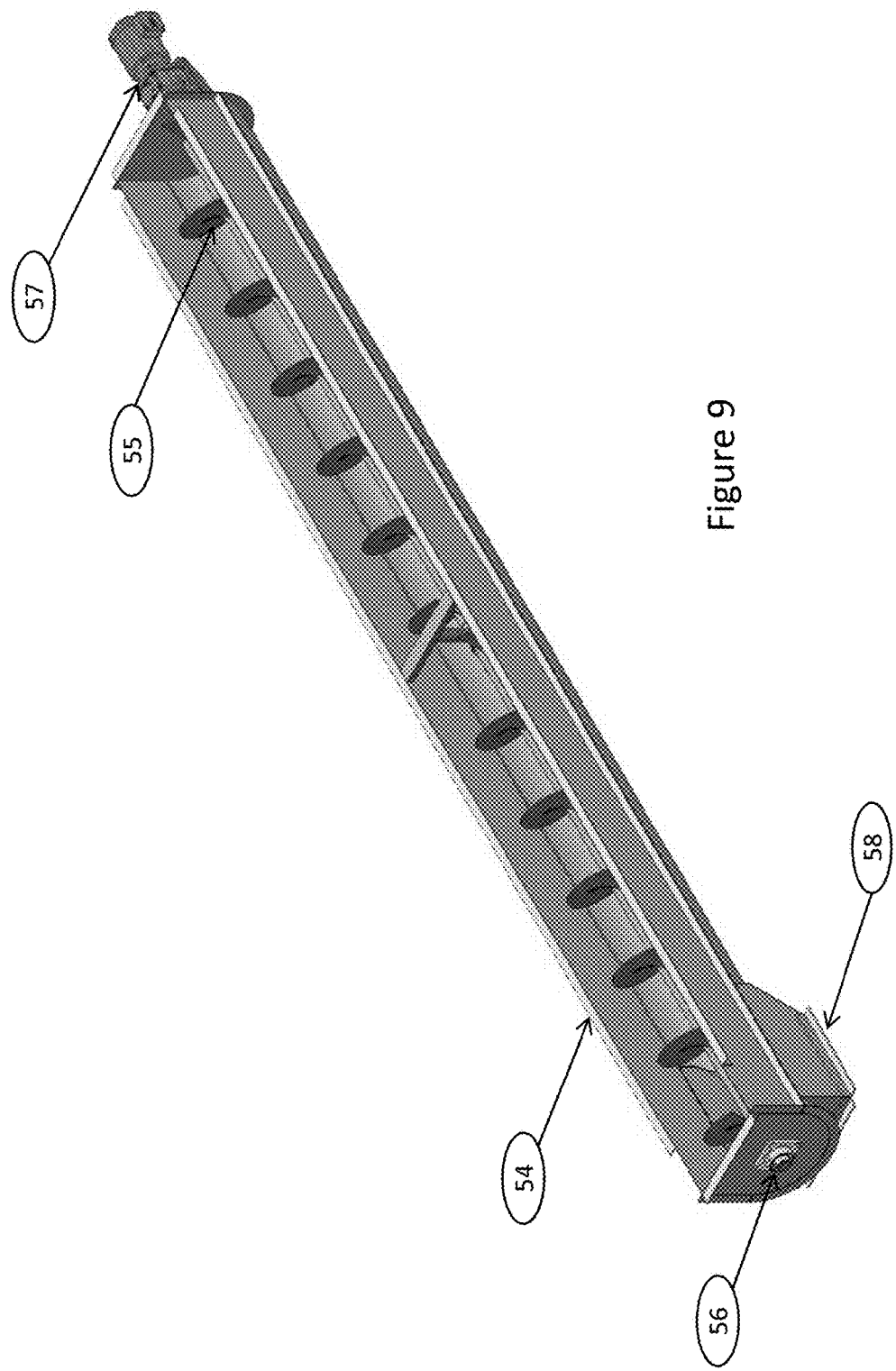
FIG. 9 corresponds to an overview of the inclined conveyor used to transport the sterilized material to a live bottom vessel.

Once the sterilization process is completed, the material is evacuated through the sterilizers discharge conveyor system of FIG. 8, which corresponds to an auger conveyor having a main body 42 where a continuous helical auger 43 is located supported on the ends of the conveyor on two bearings 44 and driving the rotating auger for receiving the sterilized fruit and digested material from the sterilizers for delivery to the inclined conveyor of FIG. 9 through an outlet 46.

Figure 10:
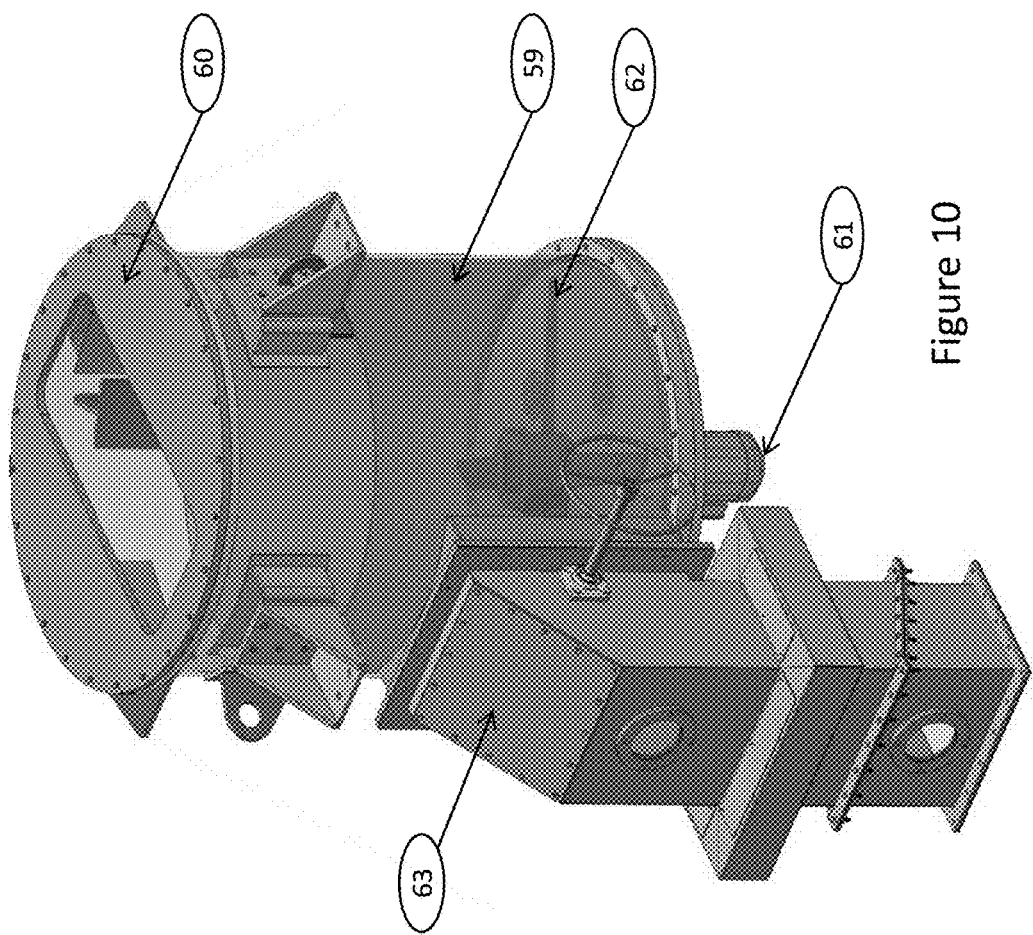
FIG. 10 corresponds to a diagram of a live bottom vessel.

Said inclined conveyor of FIG. 9 is of the auger conveyor type and it has a main body 54 inside of which an auger core shaft 55 which is supported at its ends by means of bearings 56 and is coupled to a gearmotor 57 whose rotation allows to move the material from the previous conveyor to the top of the press structure. The inclined conveyor finally delivers the material received through an outlet 58 to the live bottom vessel of FIG. 10, which is a cylindrical container vertically disposed on a metallic structure, the main body 59 has at the top an intake cap 60 which receives the material provided by the inclined conveyor of FIG. 9, while the lower part has one gearmotor 61 attached which rotates a sweeper arm 62 to evacuate the material received through a metering container 63, which in turn delivers the material to the red oil press of FIG. 11.

Eventually, steam injection elements may be adapted to said live bottom vessel if required to heat the fruit.

Figure 11:
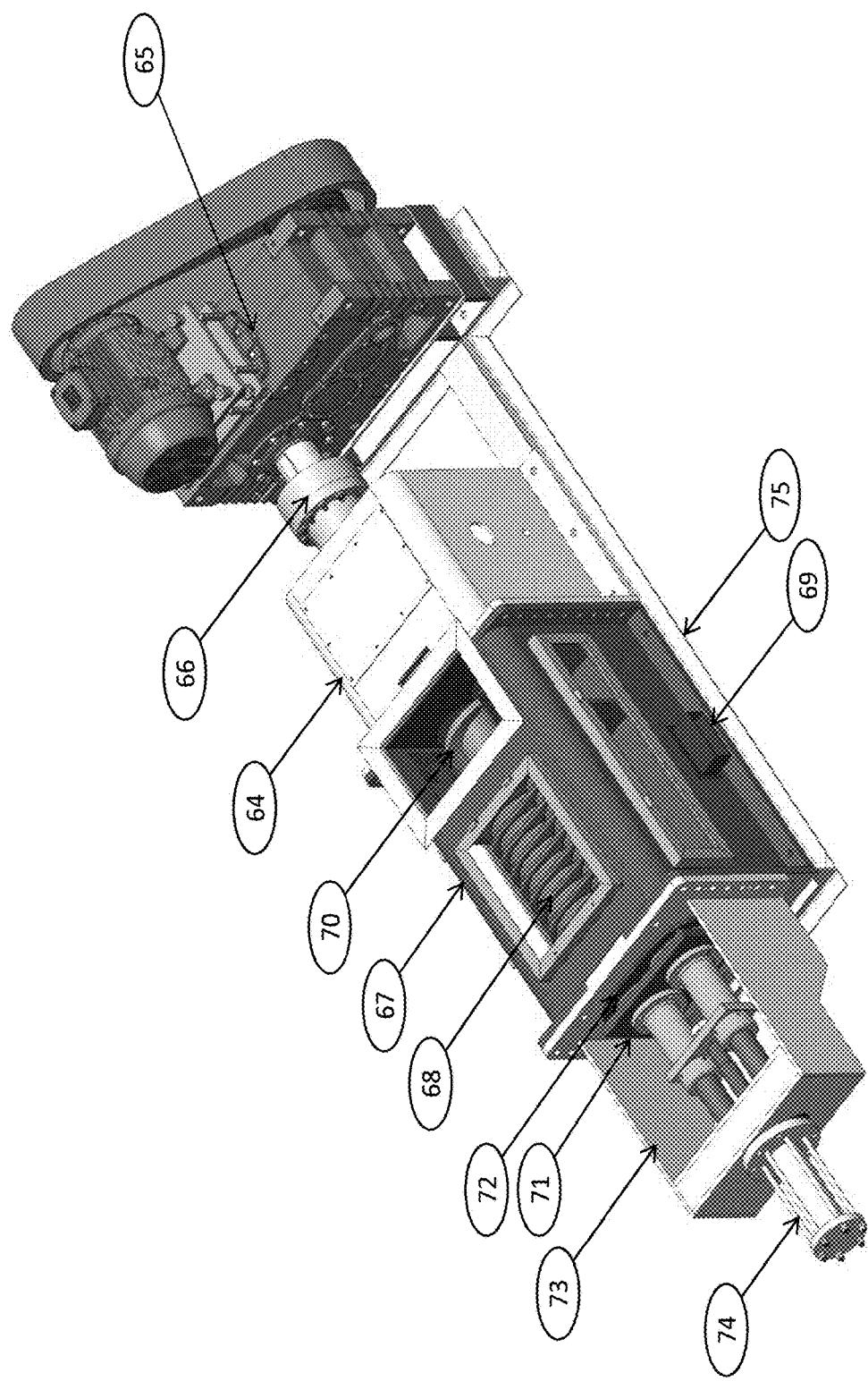
FIG. 11 corresponds to a diagram of the red oil extraction press.

The red oil extraction press of FIG. 11 has the function of mechanically compressing the sterilized fruit and digested material to be under high pressure, further obtaining a liquid phase and a solid phase. The main body of said extraction press is formed by a transmission housing 64 into which two parallel shafts transmitting the rotary motion provided by the gearmotor 65 through the coupling 66 are provided. On the other hand, the transmission housing is connected to a basket carrier housing 67 that is a metal structure that supports inside a perforated basket 68 responsible for receiving through their holes the liquid phase of the process (called press liquor), which is drained by the outlet nozzle 69 to the vibrating screen of FIG. 12.

Inside the perforated basket 68 two pressing helical augers 70 are placed whose function is to press the material against a back pressure plate 71 for extracting the liquid phase and remove the total fibers from the press through the exit ring of the basket carrier housing 72 that is further configured to support the perforated basket 68. On the other hand, the system backpressure is installed above the hydraulic housing 73 where in turn a hydraulic cylinder 74 is located, that by the action of a pressure regulatory system allows controlling pressure on the fibers for obtaining a cake made of total fibers and fruit nuts in the best conditions of the process. All components of the press are located and supported on a structure or frame 75.

Figure 13:
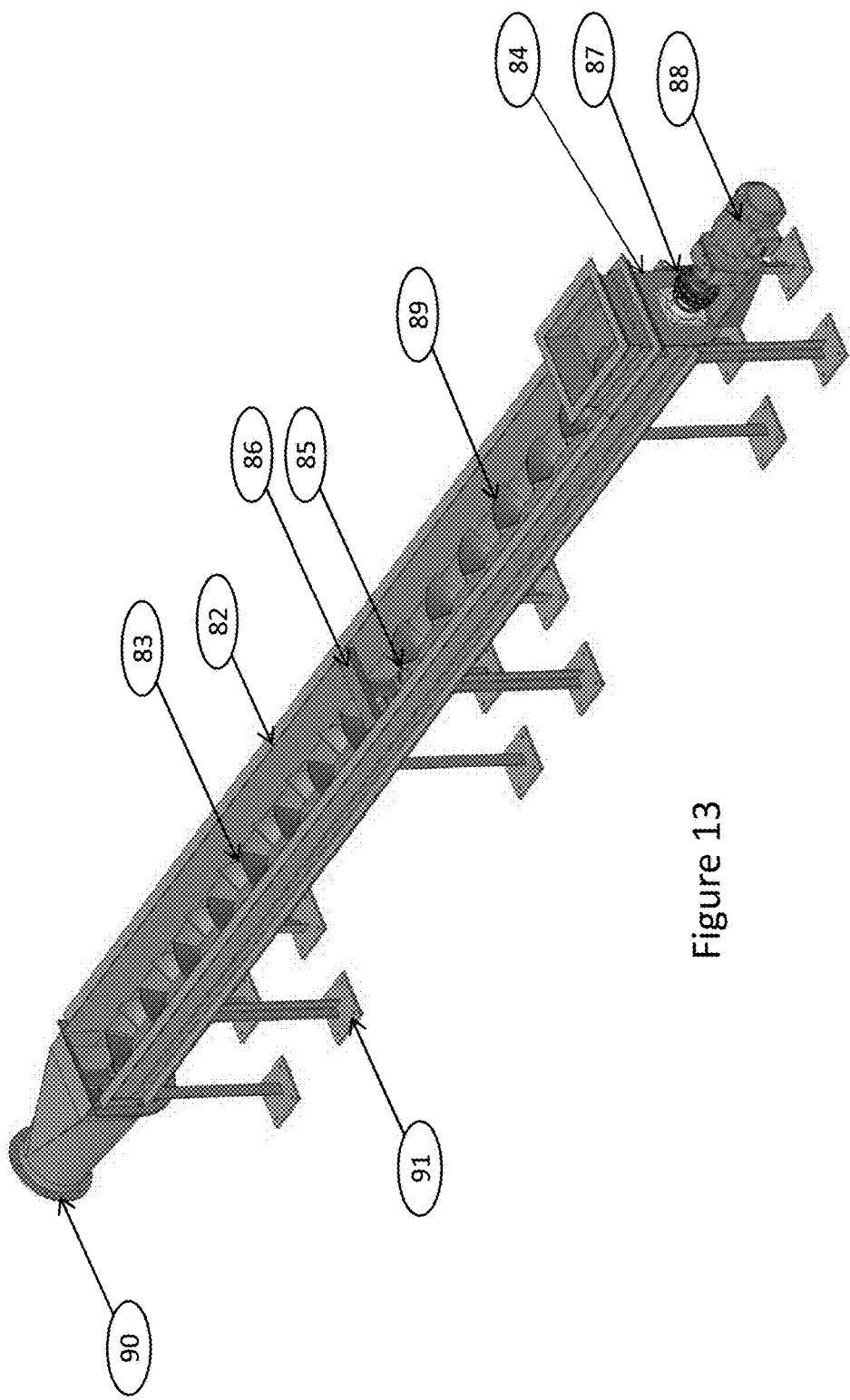
FIG. 13 corresponds to a diagram of the cake conveyor dryers.

Finally, the press unloads the solid phase by gravity sending the pressing cake to the conveyor dryer of FIG. 13.

Figure 12:
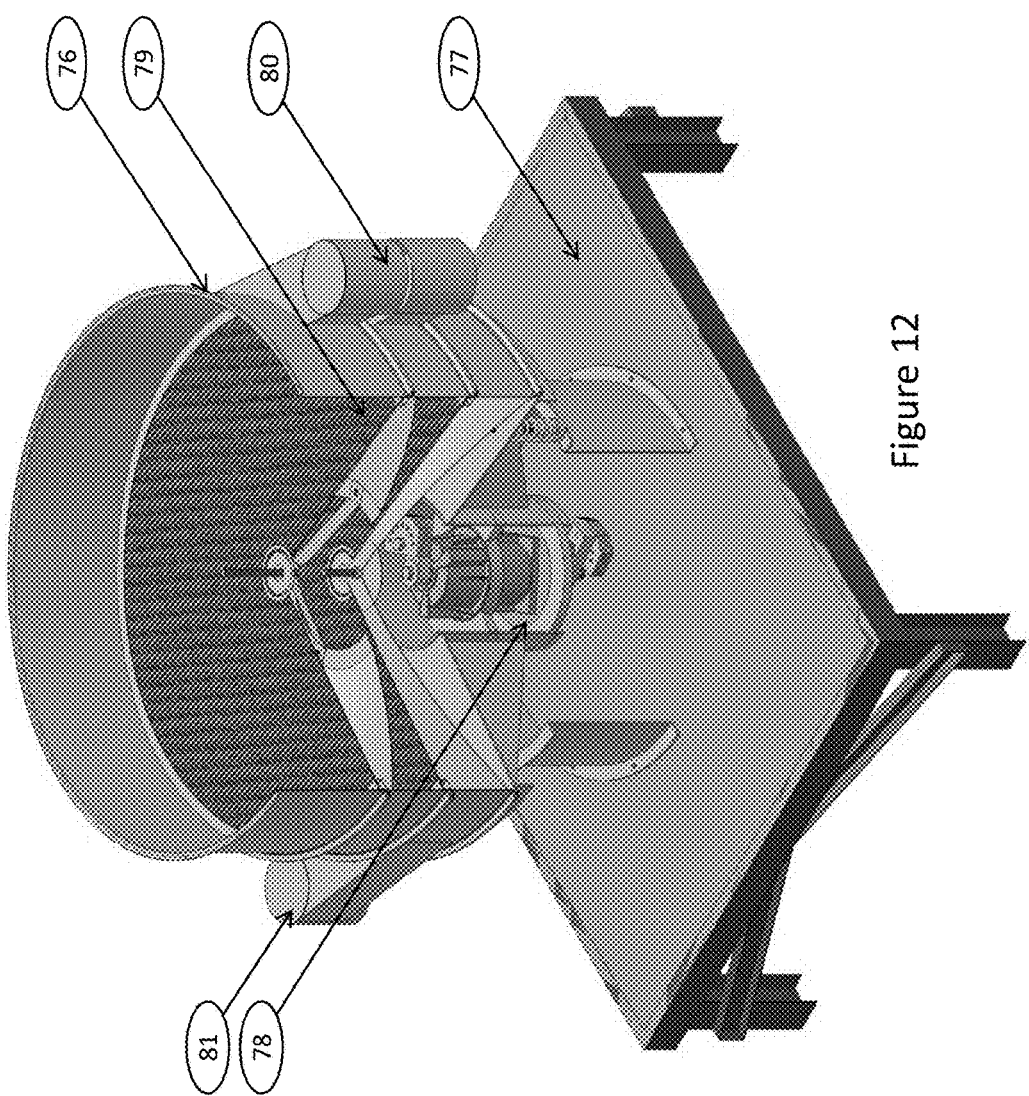
FIG. 12 corresponds to a diagram of the vibrating screen.

As previously mentioned, the vibrating screen of FIG. 12 is responsible for receiving the press liquor on its upper surface, formed by a circular container provided with a main body 76, supported on a structure 77, having inside a special eccentric motor 78 to vibrate the circular screens 79 and laterally comprises two nozzles 80 through which the obtained solids are discharged at the reprocessing of pressing.

Finally, the screened press liquor is drained from the outlet nozzle 81 to be discharged over the container of the pre-clarifier for the oil-water separation process.

Now, the cake conveyor dryer of FIG. 13 is configured to receive the cake from the press and move towards the outlet of the system. However, during the path, cake is stirred by the action of a series of inclined blades in order to reduce the moisture content of the same.

Said conveyor cake dryer has a main body 82 formed by a sheet and profiles structure inside which a round shaft 83 is placed which is supported at the ends by means of bearings 85 due to its extreme length. Said supports are connected to the main body by hangers 86, while an end is connected via a coupling 87 to a gearmotor 88. The rotary action of the gearmotor rotates the shaft that contains metal fins 89 installed on its surface, which, by being properly inclined allow stirring and moving the cake along its body for reducing humidity and separate fibers from nuts facilitating their further separation.

Figure 14:
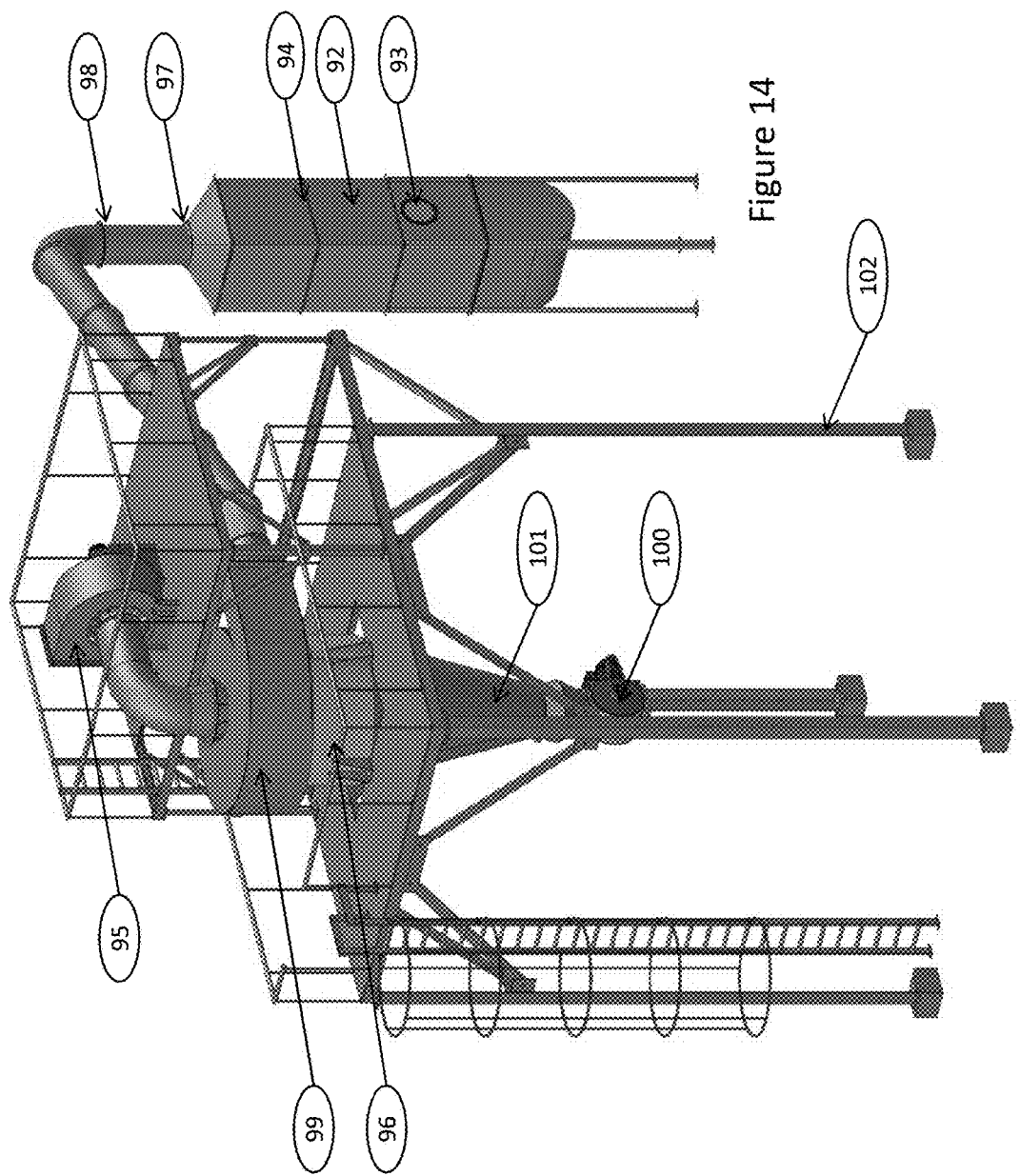
FIG. 14 shows a diagram of an air separation column.

The cake conveyor dryer finally delivers the treated product through outlet 90 to the air separation column of FIG. 14. Said conveyor dryer product may be arranged horizontally or in an inclined manner, and also may be supported on supporting bases 91.

The air separation column of FIG. 14 is a rectangular container located vertically, and whose function is to receive the fragmented cake to separate fibers and fruit nuts. Said separation column is formed by a rectangular main body 92 which in turn is provided with an inlet 93 and inside includes a set of baffles 94 which allow fluidizing air flow generated by fan 95 located on the cyclone 96, where the latter is supported on a support structure 102.

Additionally, the top of the main body has a circular nozzle 97 which is connected to the fiber evacuation pipe 98 and is responsible for delivering the fibers displaced by the air stream to the cyclone via the cyclone inlet nozzle 99. Fibers separated from nuts are stored in the cyclone and are discharged therefrom through an airlock 100 placed at the end of the cyclone cone 101.

Figure 15:
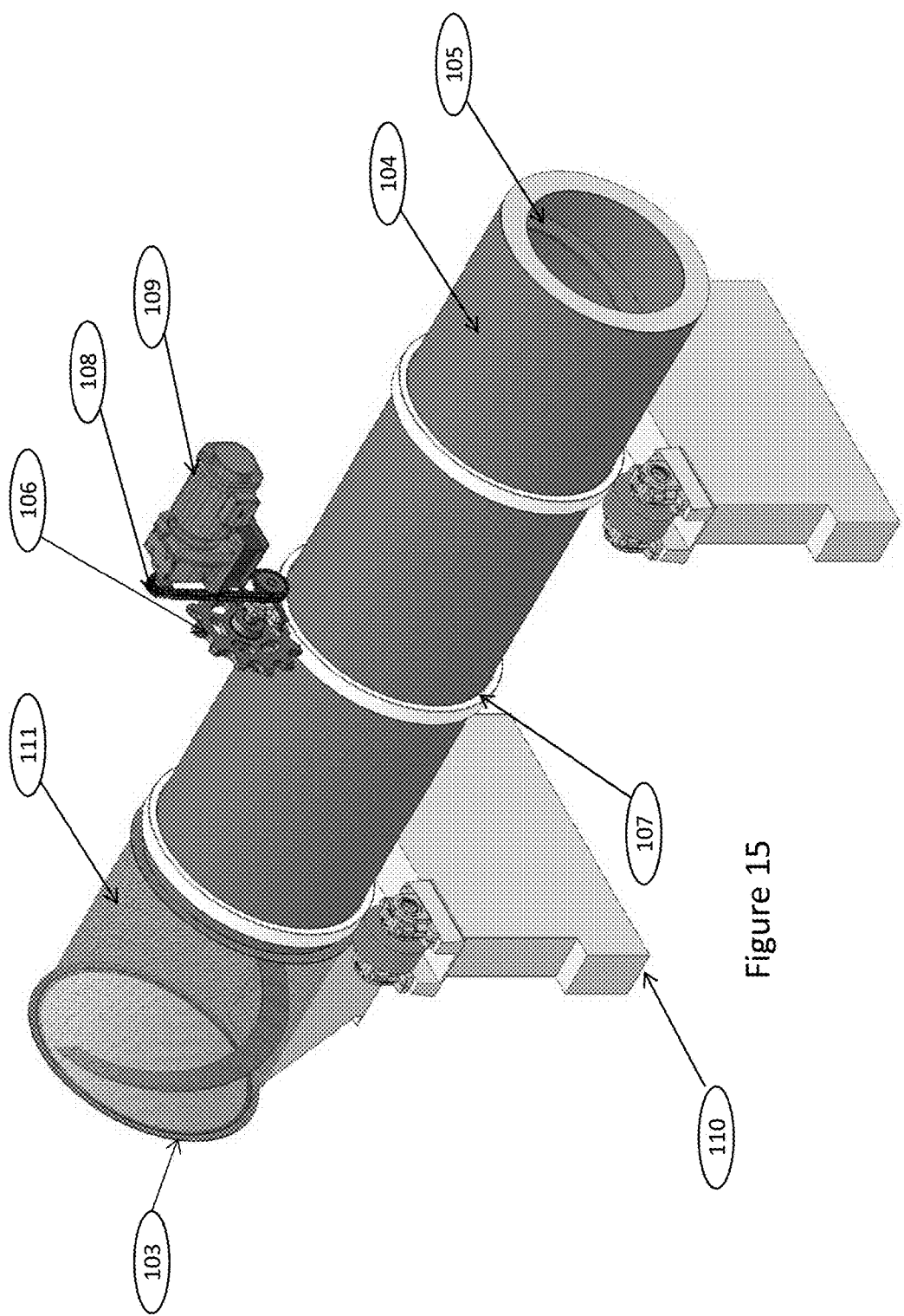
FIG. 15 corresponds to a diagram of the nut polishing drum.

Fibers evacuated from cyclone 96 are intended for use as biomass or boiler fuel, or may be used as organic material for composting processes. On the other hand, the nuts, by being more dense than the fibers are deposited on the lower part of the air separation column where there is a circular outlet nozzle towards the nut polishing drum of FIG. 15, which is a rotating equipment that is coupled in the lower part of the air column through an attachment nozzle 103.

The main body 104 of said polishing drum is cylindrical and inside there is a screw 105 which extracts nuts from the bottom of the air separation column and moves them along the body of the polishing drum in which by rotation and friction with each other they are polished, removing small fibers that facilitate further processing.

On the other hand, in the external body of the nut polishing drum a gear 106 is located, which is actuated by a chain 107 which in turn is connected by another pinion 108 to a gearmotor 109, thereby producing the rotational movement of the polishing drum. Said polishing drum is supported on metal pedestals 110.

Nuts are discharged from the polishing drum by its outlet. On the other hand, fibers arising from the nuts are discharged through the holes of the circular mesh 111 that form the body of the drum.

Figure 16:
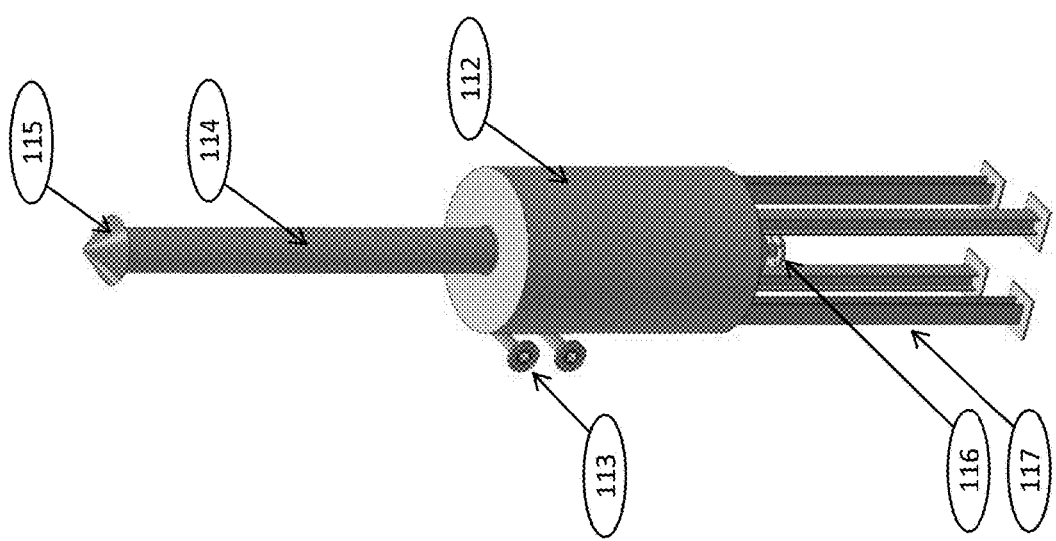
FIG. 16 corresponds to a diagram of the steam condenser.

Finally, the system for palm oil extraction disclosed in the present invention comprises a steam condenser (FIG. 16), which is a vertical cylindrical vessel arranged to receive the vapor discharge of the dynamic sterilizers, and is formed by a main body 112 which is made of steel and has several side entries 113 that allow the entry of steam. Additionally, said steam condenser has on its upper part a large height vertical cylinder 114 provided with a conical cap 115, while the lower part has a flanged outlet 116 to evacuate the steam condensates. Said condenser is supported on a profile structure 117.

Figure 17:
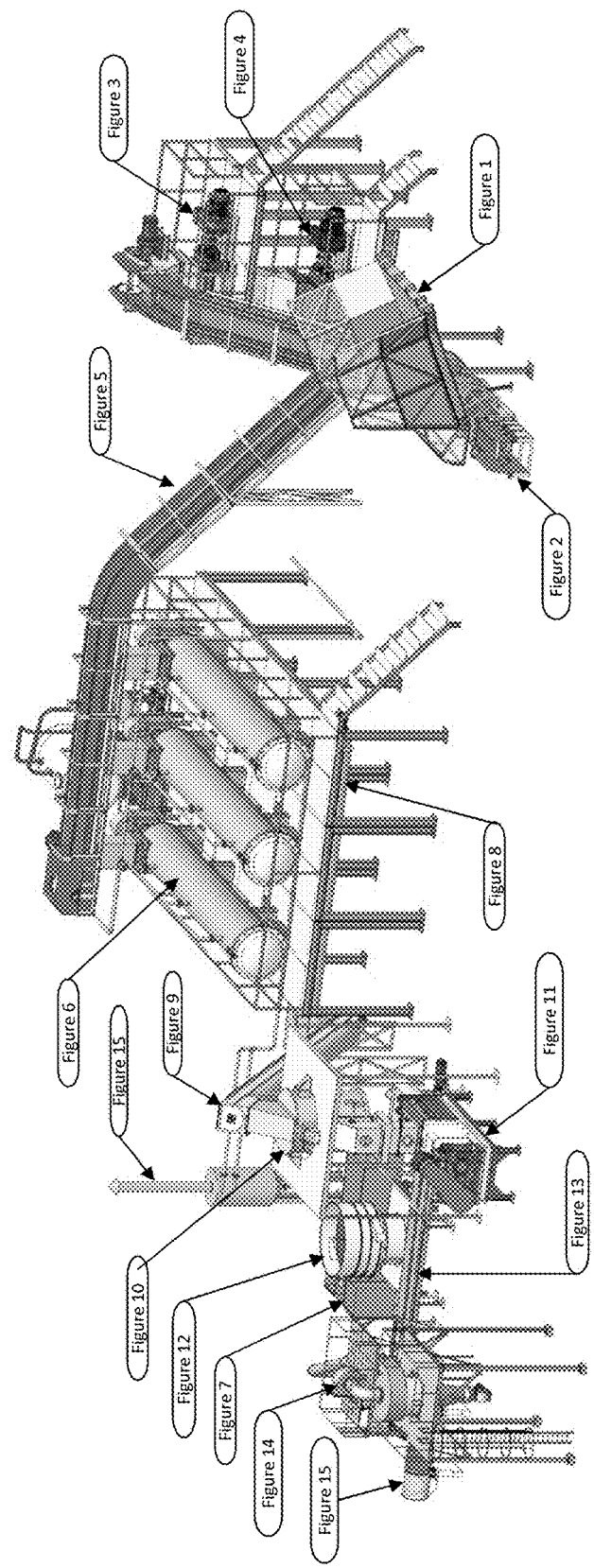
FIG. 17 is a general schematic view of the system for palm oil extraction disclosed in the present invention; and, FIG. 18 is a flowchart showing in a condensed manner the stages of the process for extracting palm oil disclosed in the present invention.

FIG. 17 shows a schematic view of all the elements for the palm oil extraction system disclosed in the present invention, being able to see in detail the manner in which each of said elements is arranged in the system.

Figure 18:
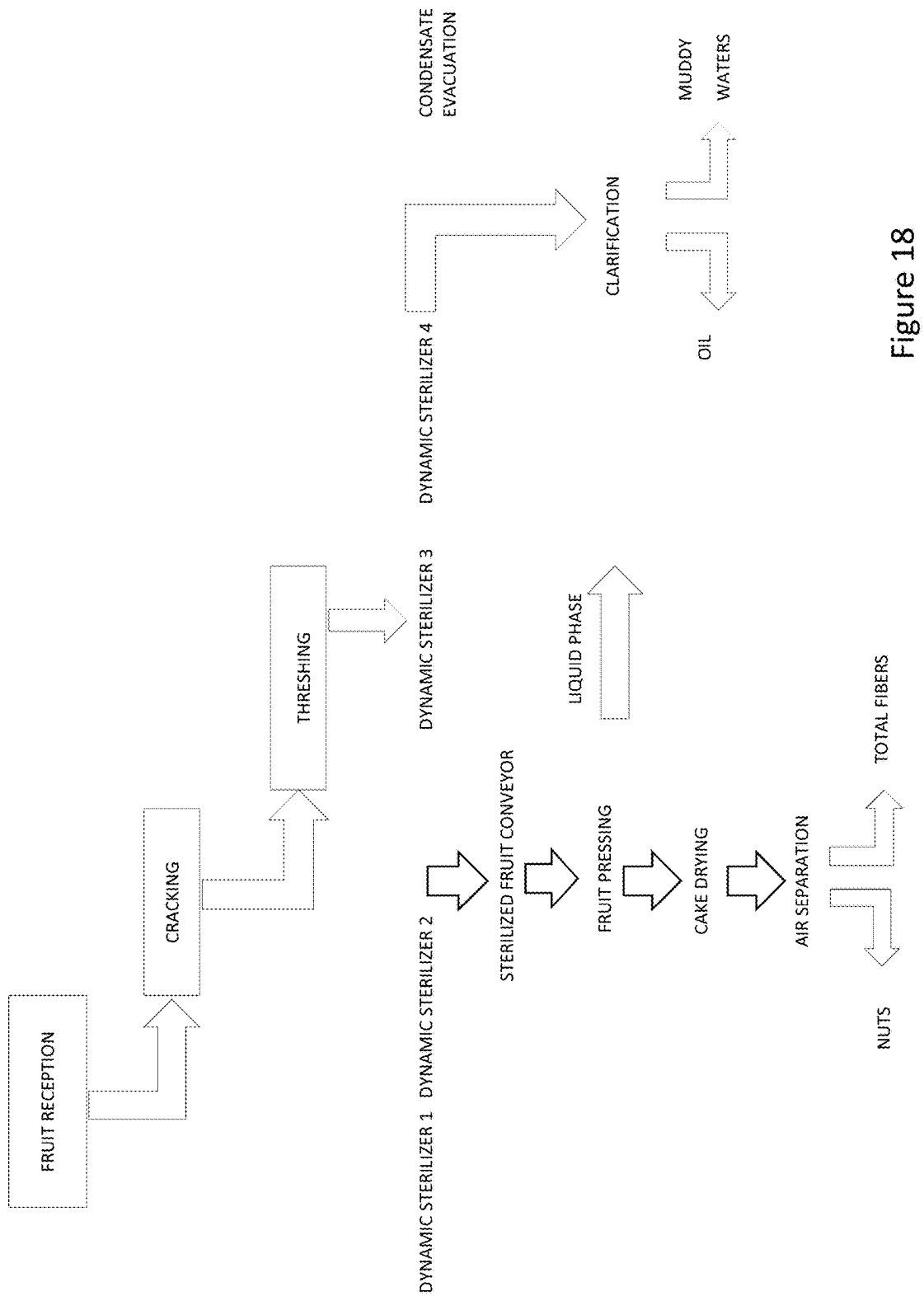

On the other hand, FIG. 18 shows a flowchart indicating in a summarized manner the different stages comprising the process for extracting palm oil disclosed in the present invention.

Comparative Tests

Comparative experimental tests were conducted between a palm oil extraction process using: i) the conventional method, ii) the dynamic method disclosed in Colombian patent CO 09-100228 and iii) the method disclosed in the present invention, monitoring a series technical aspects and features for each case, as shown below:

a) Requirements in plant covered area by taking a plant size for a capacity of 10 tonnes of fresh fruit per hour:

| CONVENTIONAL SYSTEM | PATENT | DISCLOSED METHOD | VARIATION/ CONVENTIONAL |
| --- | --- | --- | --- |
| 5320 $M^2$ | 2500 $M^2$ | 2000 $M^2$ | 62% | b) Electricity consumption per tonne:

| CONVENTIONAL SYSTEM | PATENT | DISCLOSED METHOD | VARIATION/ CONVENTIONAL |
| --- | --- | --- | --- |
| 20 KW/TON | 22 KW/TON | 16 KW/TON | 20% | c) Water consumption per ton processed

| CONVENTIONAL SYSTEM | PATENT | DISCLOSED METHOD | VARIATION/ CONVENTIONAL |
| --- | --- | --- | --- |
| 800 L | 300 L | 200 L | 75% | d) Time of sterilization and digestion process

| CONVENTIONAL SYSTEM | PATENT | DISCLOSED METHOD | VARIATION/ CONVENTIONAL |
|---|---|---|---|
| 90 MIN. | 30 MIN. | 30 MIN. | 66% | e) Percentage of total oil loss

| CONVENTIONAL SYSTEM | PATENT | DISCLOSED METHOD | VARIATION/ CONVENTIONAL |
|---|---|---|---|
| 2% | 1.50% | 1% | 50% | f) Loss of oil in pressing fibers measured as SSNA/FRUIT

| CONVENTIONAL SYSTEM | PATENT | DISCLOSED METHOD | VARIATION/ CONVENTIONAL |
|---|---|---|---|
| 8% | 6.00% | 4.50% | 43.75% | g) Oil acidity as free fatty acids %

| CONVENTIONAL SYSTEM | PATENT | DISCLOSED METHOD | VARIATION/ CONVENTIONAL |
|---|---|---|---|
| 3% | 4% | 2.2% | NORMAL | h) Oil quality (measured as peroxides active $O_2$/kg oil)

| CONVENTIONAL SYSTEM | PATENT | DISCLOSED METHOD | VARIATION/ CONVENTIONAL |
|---|---|---|---|
| 5% | 6% | 2.5% | 50% | i) Pressing cake humidity

| CONVENTIONAL SYSTEM | PATENT | DISCLOSED METHOD | VARIATION/ CONVENTIONAL |
|---|---|---|---|
| 35% | 30% | 20% | 43% | j) Obtainment of available biomass

| CONVENTIONAL SYSTEM | PATENT | DISCLOSED METHOD | VARIATION/ CONVENTIONAL |
|---|---|---|---|
| 10% | 25% | 30% | 300% | k) Reduction of the amount of equipment required for oil extraction

Comparing the conventional process and the patent the use of the following components is removed.
Conventional System:
  Rail System
  Rail wagons
  Tractors for moving trucks or mechanical system
  Rail wagon turners
  Threshing drum
  Evacuation band of empty cobs
  Cob press
  Tank for liquids obtained from the cob
  Condensate channels
  Florentine tanks
  Digester
System Reported in Colombian Patent 09-100228 CO
  Grid for separation of chopped rachis and fruit
  Pressing rollers for chopped rachis
  Double gates of the sterilizer From the above it is evident that the system and method disclosed in the present invention allow obtaining clear technical advantages over the systems and methods known in the prior art for palm oil extraction.

The invention claimed is:

1. A system for palm oil extraction characterized by comprising:
a metering hopper for fresh fruit, having an outlet for delivering a result to a conveyor configured for delivering fruits to a cracking apparatus, after which cracked material is transferred to a grid separating detached fruits and delivers cracked bunches to a threshing apparatus as a previous step for cracked and threshed material to be transported by a conveyor to a battery of dynamic sterilizers, inside which there is a combined system of augers that by rotation deliver at an outlet of sterilizers sterilized and digested material to a helical auger type conveyor having an outlet through which sterilized product goes to an inclined conveyor.

2. The system for extracting oil of claim 1, further characterized in that the dynamic sterilizers, have inputs arranged for injecting steam and outlets for condensate discharge that are delivered to pre-clarifier as wells as steam evacuation outlets that are discharged into a steam condenser.

3. The system for extracting oil of claim 1 further characterized in that the inclined conveyor includes an output which delivers received material to a live bottom vessel, which in turn delivers a product to a red oil extraction press, wherein a processed material is fractionated into its liquid and solid phase.

4. The system for extracting oil of claim 1, further characterized by comprising a cake conveyor dryer for drying a cake, and a vibrating screen which is configured for screening a press liquor and is further configured to obtain solids that are reprocessed and screened to obtain a press liquor that is discharged to a pre-clarifier.

5. The system for extracting oil of claim 1, characterized by comprising an air separation column, for fibers and nuts that obtains fibers in a cyclone and nuts in a polishing drum.

6. The system for extracting palm oil of claim 1, characterized in that it comprises a pre-clarification system where palm oil and muddy waters for treatment are obtained.

7. The system for extracting palm oil of claim 1, characterized in that the sterilizer contains on an inside a set of helical augers with two different sizes and orientations that allows bringing a product to a continuous movement during the sterilization process.

8. The system for extracting palm oil of claim 1 characterized in that the cracking apparatus comprises two rotating shafts and a central blade that allows cracking a whole bunch and the threshing apparatus is equipped with a set of shafts with metallic nails that rotate on themselves at a big difference in speeds allowing to thresh fruits from cracked bunches.

9. The system of claim 1, characterized in that a sterilization is performed using an amount of sterilizers that are necessary to achieve a continuous sterilization process.

10. A process for palm oil extraction comprising the stages of:

a) receiving and dosing a whole fruit to a conveyor by means of a hopper;
b) providing bunches from the conveyor of step a) to a bunch cracking apparatus;
c) passing the cracked material of step b) through a fixed grid, separating detached fruits and cracked bunches;
d) threshing cracked bunches of step c);
e) transporting 100% of the product obtained in step d) and the detached fruits of step c) to a battery of sterilizers;
f) sterilizing threshed fruit along with chopped rachis with constant dynamic movements in dynamic sterilizers;
p) perform in the dynamic sterilizers of step f) a digestion process; and
h) supplying sterilized and digested fruit of step g) to one or more presses for oil extraction for obtaining press liquor and press cake.

11. The process of claim 10 characterized in that comprises cracking a whole bunch and threshing the whole bunch.

12. The process of claim 10, characterized in that a sterilization and digestion of cracked and threshed fruit is performed under temperature conditions between 110 to 150 centigrade degrees and pressure between 30 to 60 psi.

13. The process of claim 10, characterized by comprising a stage of pre-clarification of the press liquor for obtaining oil and muddy waters.

14. The process of claim 10, characterized by comprising the cake drying and separation of fibers and nuts.

15. The process of claim 10, characterized in that the sterilization and digestion of the fruit is made simultaneously in the dynamic sterilizers.

16. The process of claim 10, characterized in that a pressing for palm oil extraction is made to 100% of the fruit.

17. The process of claim 10, characterized in that a dynamic sterilization is carried out using an amount of sterilizers necessary for achieving a continuous sterilization process.

* * * * *